(12) United States Patent
Barman et al.

(10) Patent No.: US 9,901,544 B2
(45) Date of Patent: Feb. 27, 2018

(54) MEMBRANE-ADHERENT SELF-ASSEMBLED SYSTEM FOR TREATMENT OF OCULAR DISORDERS

(71) Applicant: Integral Biosystems LLC, Bedford, MA (US)

(72) Inventors: Shikha P Barman, Bedford, MA (US); Kevin L. Ward, Arlington, MA (US); Anne-Marie Cromwick, Saugus, MA (US); Koushik Barman, Bedford, MA (US); Ritesh V. Thekkedath, Boston, MA (US)

(73) Assignee: Integral Biosystems LLC, Bedford, MA (US)

(*) Notice: Subject to any disclaimer, the term of this patent is extended or adjusted under 35 U.S.C. 154(b) by 0 days.

(21) Appl. No.: 15/308,000

(22) PCT Filed: May 1, 2015

(86) PCT No.: PCT/US2015/028748
§ 371 (c)(1),
(2) Date: Oct. 31, 2016

(87) PCT Pub. No.: WO2015/168523
PCT Pub. Date: Nov. 5, 2015

(65) Prior Publication Data
US 2017/0049697 A1    Feb. 23, 2017

Related U.S. Application Data

(60) Provisional application No. 61/987,012, filed on May 1, 2014.

(51) Int. Cl.
| | | |
|---|---|---|
| *A61K 9/00* | (2006.01) | |
| *A61K 47/10* | (2017.01) | |
| *A61K 47/24* | (2006.01) | |
| *A61K 47/36* | (2006.01) | |
| *A61K 47/44* | (2017.01) | |
| *A61K 9/10* | (2006.01) | |
| *A61K 31/4709* | (2006.01) | |
| *A61K 31/56* | (2006.01) | |
| *A61K 31/573* | (2006.01) | |
| *A61K 47/14* | (2017.01) | |

(52) U.S. Cl.
CPC ............. *A61K 9/0048* (2013.01); *A61K 9/10* (2013.01); *A61K 31/4709* (2013.01); *A61K 31/56* (2013.01); *A61K 31/573* (2013.01); *A61K 47/10* (2013.01); *A61K 47/14* (2013.01); *A61K 47/24* (2013.01); *A61K 47/36* (2013.01); *A61K 47/44* (2013.01)

(58) Field of Classification Search
CPC .................................................. A61K 9/0048
See application file for complete search history.

*Primary Examiner* — Noble E Jarrell
*Assistant Examiner* — John S Kenyon
(74) *Attorney, Agent, or Firm* — Cesari and McKenna, LLP

(57) ABSTRACT

A liquid crystalline drug delivery system for ocular administration. The drug delivery system, which is mucoadhesive, biocompatible, non-irritating, and tissue permeable, contains nanoparticles stably dispersed in an aqueous solution and can be formulated for sustained release. Also provided are methods for producing the drug delivery system and methods for treating ocular disorders by administering it to a subject.

20 Claims, No Drawings

MEMBRANE-ADHERENT SELF-ASSEMBLED SYSTEM FOR TREATMENT OF OCULAR DISORDERS

CROSS REFERENCE TO RELATED APPLICATIONS

This application is the National Stage of International Application No. PCT/US/2015/028748, filed on May 1, 2015, which claims the benefit of U.S. Provisional Application Ser. No. 61/987,012, filed on May 1, 2014. The contents of both applications are hereby incorporated by reference in their entirety.

BACKGROUND

Field

The application relates to nanostructured dispersions that can be used to effectively treat disorders and diseases of the eye by administering the dispersions on the ocular surface, in the anterior chamber, and in the posterior chamber.

Background Information

Many ophthalmic formulations include drug crystals suspended in ointments which are composed of mineral oil and petrolatum. Such formulations often result in irritation of the eye and patient non-compliance due to blurry vision and inconvenience. Other ophthalmic formulations are eye-drops containing drug suspensions in an aqueous solution, some of them viscous to extend residence time on the ocular surface.

The effective use of eye-drops is limited by the fact that many therapeutically valuable agents cause local irritation when topically dosed to the eye. The cornea is highly sensitive to the application of chemical agents. As such, this sensitivity significantly limits the use of many otherwise valuable therapeutic agents.

Another issue with existing ocular drug formulations is poor bioavailability of the drug. For example, poorly soluble drugs delivered to the front of the eye as a suspension, e.g., eye drops, must dissolve prior to being absorbed into the eye by diffusion. Problematically, the rate of drug dissolution is typically much slower than the rate of fluid clearance from the ocular surface. Thus, ineffective drug absorption, i.e., poor bioavailability, is one of the issues that confounds front-of-the-eye drug delivery.

To address this issue, insoluble or poorly soluble drugs, e.g., prostaglandins and difluprednate, are typically dissolved in an organic excipient followed by emulsification in an aqueous vehicle. The use of emulsions frequently leads to irritation of the ocular surface, resulting from the use of excipients that cause ocular surface inflammation. This is especially true when the medication is utilized for chronic ocular surface disease therapies, such as therapies for glaucoma, dry eye, and allergies.

Further, emulsions are inherently unstable, resulting in coalescence and subsequent separation of the phases.

The issues are different for back-of-the-eye diseases. For example, drug suspensions of triamcinolone acetonide have been injected intravitreally to alleviate inflammation resulting from diabetic macular edema. Multiple injections into the posterior segments of the eye can cause endophthalmitis and gradual retinal detachment.

The need exists for formulations for ocular administration which are non-irritating, stable, and capable of delivering a drug at therapeutic concentrations for an extended period. Additionally, a sustained release delivery system that is non-toxic and membrane-mimetic is needed for the treatment of back-of-the-eye diseases.

SUMMARY

To meet the needs discussed above, a liquid crystalline drug delivery system is provided. The system contains nanoparticles having a size of 40-900 nm dispersed in an aqueous solution. The nanoparticles include a lipidic component and an alcohol. The aqueous solution contains a mucoadhesive hydrophilic polymer and a buffer.

The lipidic component is present at 0.1-1% by weight of the system and the alcohol is present at 0.1-5% by weight of the system. The mucoadhesive hydrophilic polymer is present at 1-5% by weight of the system.

A method for producing the liquid crystalline drug delivery system is also disclosed. The method includes the following steps: (i) forming a first solution containing a lipidic component and an alcohol, the first solution being maintained at a first temperature; (ii) obtaining a second solution that includes a mucoadhesive hydrophilic polymer and a buffer, the second solution being aqueous and maintained at a second temperature; (iii) mixing the first solution and the second solution to form a combined nano/microdispersion, the mixing accomplished by a high energy mixing process; (iv) subjecting the combined nano/microdispersion to microfluidization at a third temperature to form a nano-dispersion; and (v) incubating the nano-dispersion at 2-5° C. to form a liquid crystalline drug delivery system.

In the method disclosed above, the first solution and the second solution are mixed at a weight ratio of 1:1 to 1:15.

Additionally provided is a liquid crystalline drug delivery system produced by the above-described method.

Further, a method for treating an ocular disorder in a subject is disclosed including the steps of identifying a subject having an ocular disorder and administering to an eye of the subject the liquid crystalline drug delivery system described above.

In another aspect, the use of the liquid crystalline drug delivery system in the manufacture of a medicament for treating ocular disorders is disclosed.

The details of one or more embodiments of the invention are set forth in the drawings and description below. Other features, objects, and advantages of the invention will be apparent from the description and from the claims. The contents of all documents cited herein are hereby incorporated by reference in their entirety.

DETAILED DESCRIPTION

As mentioned above, the liquid crystalline drug delivery system includes nanoparticles dispersed in an aqueous solution. The delivery system has a unique internal morphology that contains poorly soluble drug molecules dissolved in its interstices for sustained release and absorption, resulting in greater bioavailability than is possible with suspensions. Both hydrophilic and hydrophobic drugs can be incorporated into the liquid crystalline delivery system, either individually or in combination.

The delivery system is a biphasic liquid, with a nanoparticle phase contained with a continuous aqueous phase. The drug is dissolved in the nanoparticle phase, which contains both hydrophilic and hydrophobic components. When mixed together, the phases interact with one another to form a liquid crystalline phase. The interaction between the nanoparticle phase and the continuous phase display the unique characteristics of an ordered nanostructured assembly. The phases separately are not ordered or liquid crystalline.

A liquid crystalline phase is defined as a state of matter having properties between a conventional liquid and a solid crystal. A liquid crystal may flow like a liquid, but its molecules may exist in crystal-like orientations. A liquid crystalline phase, when viewed under an optical microscope under crossed polarizers, will display multicolored textures, i.e., birefringence. Liquid crystalline phases also have distinct melt transitions when heated, as determined by differential scanning calorimetry X-ray diffraction techniques cane also used to characterize liquid crystals, due to the ability of crystals to display the Bragg reflection of light.

The liquid crystalline drug delivery system contains nanoparticles with sizes from 40 nm-900 nm, which can easily permeate through all tissues of the eye, such the cornea and the sclera. The delivery system is designed to be mucoadhesive, to enhance residence time on the ocular surface.

As mentioned above, the liquid crystalline drug delivery system includes nanoparticles dispersed in an aqueous solution. As also mentioned above, the nanoparticles include a lipidic component and an alcohol. The lipidic component can include, e.g., phosphatidylcholine and medium chain triglycerides. The alcohol can be cetyl alcohol.

The nanoparticles can also include one or more of cholesterol, glycerol, polyethylene glycol (PEG) 400, polypropylene glycol (PPG), PEG-stearate, poloxamer 407, tyloxapol, polysorbate 80, castor oil, and PEGylated castor oil. Additionally, polymers such as poly(lactic-co-glycolic acid) (PLGA) can be included in the nanoparticles for sustained release formulations.

In one embodiment, the nanoparticles include phosphatidylcholine, medium chain triglycerides, and cetyl alcohol. In another embodiment, the nanoparticles include phosphatidylcholine, medium chain triglycerides, cholesterol, and cetyl alcohol.

The aqueous solution mentioned above contains a mucoadhesive hydrophilic polymer. The polymer can be, but is not limited to, sodium hyaluronate, xanthan gum, guar gum, carboxymethylcellulose, albumin, hydroxypropylcellulose, polyethylene glycol, polyethyleneimine, mucin, 1-4 beta glucan, poly(ethylene oxide)-poly(propylene oxide)-poly(ethylene oxide), tamarind seed polysaccharide, sodium alginate, polycarbopol, and polycarbophil, or derivatives and mixtures thereof.

The aqueous solution also contains a buffer. The buffer can be, but is not limited to, sodium acetate, sodium dihydrogen phosphate, disodium hydrogen phosphate, potassium dihydrogen phosphate, dipotassium hydrogen phosphate, $\epsilon$-aminocaproic acid; amino acid salts such as sodium glutamate, boric acid, and citric acid. Preferably, the buffer is a phosphate buffer.

In a particular embodiment of the liquid crystalline drug delivery system, the nanoparticles include phosphatidylcholine and medium chain triglycerides, cetyl alcohol, PEG-400, PPG, PEG-stearate, poloxamer 407, tyloxapol, polysorbate 80, and castor oil, and the aqueous solution contains sodium hyaluronan. In another particular embodiment, the nanoparticles include phosphatidylcholine and medium chain triglycerides, cholesterol, cetyl alcohol, PEG-400, PPG, PEG-stearate, poloxamer 407, tyloxapol, polysorbate 80, and castor oil, and the aqueous solution contains sodium hyaluronan, sodium phosphate dibasic, and sodium phosphate monobasic.

The components mentioned above can be included in the liquid crystalline drug delivery system in the following amounts, expressed as weight % of the system: 0.1-1% phosphatidylcholine and medium chain triglycerides; 0.1-5% cetyl alcohol; 0.2-2% PEG-400; 0.2-1% PPG; 0.1-0.7% PEG-stearate; 0.1-0.25% poloxamer 407; 0.01-0.15% tyloxapol; 0.01-0.02% polysorbate 80; 1-5% castor oil; 0.1-0.5% sodium hyaluronate; 0.01-0.02% sodium phosphate monobasic; 0.05% sodium phosphate dibasic, and 75-90% deionized water (dH$_2$O). An alternative liquid crystalline drug delivery system contains all of these components and also contains 0.02-0.2% cholesterol. A further embodiment includes 0.1-0.5% xanthan gum instead of the sodium hyaluronate. An additional embodiment contains 0.1-0.5% carboxymethylcellulose instead of the sodium hyaluronan.

In a specific embodiment, the liquid crystalline drug delivery system includes, by weight, 1% phosphatidylcholine and medium chain triglycerides, 1% cetyl alcohol, 2% PEG-400, 1% PPG, 1%, 0.7% PEG-stearate, 0.22% poloxamer 407, 0.10% tyloxapol, 0.10% polysorbate 80, and 3.8% castor oil, 0.14% sodium hyaluronate, 0.02% sodium phosphate monobasic; 0.05% sodium phosphate dibasic, and the balance dH$_2$O. An alternative liquid crystalline drug delivery system contains the same amounts of all these components and also contains 0.2% cholesterol.

The liquid crystalline drug delivery system described above can also contain an active pharmaceutical ingredient (API) at 0.01-0.5% by weight of the system. The API is loaded in the nanoparticles. The API can be, but is not limited to, fluticasone propionate, dexamethasone, betamethasone, budesonide, triamcinolone acetonide, methyl prednisolone, cortisone, beclometasone, fluticasone furoate, deoxycorticosterone acetate, loteprednol etabonate, difluprednate, fluorometholone, rimexolone, travoprost, moxifloxacin, prednisolone acetate, posaconazole, budesonide, netilmycin, or mupirocin.

In particular embodiments, the liquid crystalline drug delivery system includes, by weight, 0.01-0.1% fluticasone propionate, 0.01-0.1% dexamethasone, 0.01-0.1% difluprednate, 0.1-0.5% loteprednol etabonate, 0.1-0.5% posaconazole, 0.1-0.5% budesonide, 0.05-0.5% netilmycin, or 0.05-0.5% mupirocin.

In a specific embodiment, the liquid crystalline drug delivery system contains 0.1% by weight fluticasone propionate.

Each of the above-described embodiments of the liquid crystalline drug delivery system can have a pH of 6-7.5, an osmolarity of 250-340 mOsm/L, and a viscosity of 200-1000 cP.

The liquid crystalline drug delivery system described above is storage stable. For example, the nanoparticles dispersed in the aqueous solution do not settle out of the dispersion for at least 90 days.

The liquid crystalline drug delivery system can be a spray, an injectable, or formulated as eye drops. The liquid crystalline drug delivery system can be a high-viscosity liquid preloaded into a syringe.

The liquid crystalline drug delivery system disclosed herein can be produced by the following steps.

Initially, a first solution containing a lipidic component and an alcohol is formed. The lipidic component can include phosphatidylcholine and medium chain triglycerides in a preferred embodiment. The alcohol can be cetyl alcohol. After forming the solution, it can be maintained at 40-55° C. In an alternative embodiment, an API is dissolved into the first solution.

Next, a second solution, which is aqueous, is obtained that includes a mucoadhesive hydrophilic polymer and a buffer. The mucoadhesive hydrophilic polymer can be sodium hyaluronate, xanthan gum, guar gum, carboxymethylcellulose, 1-4 beta glucan, poly(ethylene oxide)-poly(propylene oxide)-poly(ethylene oxide), tamarind seed polysaccharide, sodium alginate, polycarbopol, and polycarbophil, or mixtures thereof. The buffer can be, but is not limited to, sodium acetate, sodium dihydrogen phosphate, disodium hydrogen phosphate, potassium dihydrogen phosphate, dipotassium hydrogen phosphate, ε-aminocaproic acid; amino acid salts such as sodium glutamate, boric acid, and citric acid. Preferably, the buffer is a phosphate buffer. The second solution can be maintained at a temperature of 5-55° C., preferably 40-55° C.

The first solution and the second solution are mixed together to form a combined nano/micro-dispersion. The weight ratio between the first and second solution can be 1:1 to 1:15 (e.g., 1:1, 1:2, 1:3, 1:4, 1:5, 1:6, 1:7, 1:8, 1:9, 1:10, 1:11, 1:12, 1:13, 1:4, 1:15). Preferably, the ratio is 1:9.

As mentioned above, the mixing of the first and second solutions to form a combined nano/micro-dispersion is accomplished by a high energy mixing process. The high energy mixing process can be, e.g., high shear mixing, sonication, or a combination of both processes.

The combined nano/micro-dispersion is subjected to microfluidization to form a nano-dispersion. The microfluidization can be performed, e.g., by high pressure homogenization. The microfluidization can be carried out at 40-55° C. for a period of 8-24 h.

The nano-dispersion thus formed can be incubated at 2-5° C. for a period of 12-24 h to form a liquid crystalline drug delivery system.

An alternative embodiment of the method includes, in addition to all of the aforementioned steps, a step of mixing the nano-dispersion for 16-24 h prior to incubating them at 2-5° C. for a period of 12-24 h. This mixing step can be accomplished by high shear mixing. Additionally, this mixing step can be performed at −10 to 15° C. In one embodiment, the mixing is performed at −10 to −1° C. In an alternative embodiment, the mixing is performed at 8-15° C. In another embodiment, the mixing is performed at room temperature.

The first solution mentioned above can also be formed by adding, in addition to the lipidic component and the alcohol, PEG-400, PPG, PEG-stearate, poloxamer 407, tyloxapol, polysorbate 80, and castor oil. In another embodiment, cholesterol is also added to form the first solution. In an additional embodiment, PLGA is added to the first solution.

In a particular embodiment of the method, the first solution is formed from, by weight, 10% phosphatidylcholine and medium chain triglycerides, 10% cetyl alcohol, 20% PEG-400, 10% PPG, 7% PEG-stearate, 2.2% poloxamer 407, 1% tyloxapol, 1% polysorbate 80, and 38% castor oil. The first solution can also be formed with, in addition to these components, 2% by weight cholesterol. Fluticasone propionate is dissolved into the first solution at 1%. In this particular embodiment, the second solution contains, by weight, 0.2% sodium phosphate monobasic, 0.5% sodium phosphate dibasic, and 1.5% sodium hyaluronate. The first and second solutions are mixed at a 1:9 weight ratio.

The first solution described above can be produced in a step-wise fashion. For example, an API can first be solubilized in the lipidic component and the alcohol. This solubilization can be performed at a temperature required to dissolve the desired amount of API. The temperature can be, e.g., 25-65° C. After solubilizing the API, one or more of the additional excipients described above can be added to form the first solution. The temperature of the first solution can be lowered to 30-45° C. if a higher temperature was used to solubilize the API.

As described in detail, supra, the first solution is mixed, by a high energy mixing process, with the second solution containing a mucoadhesive hydrophilic polymer. In an alternative embodiment, the mucoadhesive hydrophilic polymer is omitted from the second solution and added after the microfluidization step but before the final incubation step. This alternative process may be necessary when using specific mucoadhesive hydrophilic polymers which are sensitive to shear forces in the mixing steps.

Also mentioned above is a method for treating an ocular disorder in a subject. The method includes the steps of identifying a subject having an ocular disorder and administering to an eye of the subject the liquid crystalline drug delivery system described above.

A skilled person in the art can identify the subject having an ocular disorder by routine methods in the art, e.g., an eye exam. The ocular disorders that can be treated with the liquid crystalline drug delivery system include but are not limited to post-operative inflammation, inflammation, allergic rhinitis, allergic conjunctivitis, meibomian gland dysfunction, infection, conjunctivitis, keratitis, ulcers, blepharitis, glaucoma, uveitis, diabetic macular edema, diabetic retinopathy, age-related macular degeneration, endophthalmitis, choroidal neovascularization, tear duct dysfunction, corneal blebs, and dry eye disease.

The liquid crystalline drug delivery system can be administered to the eye by eye-drops, spray, and injection. In a particular embodiment, the liquid crystalline drug delivery system is administered by vitreous injection.

The liquid crystalline drug delivery system to be administered is preferably formulated with an API known to be effective for treating the ocular disorder. The API can be, but is not limited to fluticasone propionate, dexamethasone, betamethasone, budesonide, triamcinolone acetonide, methyl prednisolone, cortisone, beclometasone, fluticasone furoate, deoxycorticosterone acetate, loteprednol etabonate, difluprednate, fluorometholone, rimexolone, travoprost, moxifloxacin, prednisolone acetate, posaconazole, budesonide, netilmycin, or mupirocin.

In other embodiments, the liquid crystalline drug delivery system can be formulated with non-steroidal anti-inflammatory drugs, including but not limited to nepafenac, bromfenac sodium, diclofenac, flurbiprofen sodium, ketorolac tromethamine, and flurbiprofen sodium.

In another embodiment, anti-microbials can be incorporated into the liquid crystalline drug delivery system. The anti-microbials include, but are not limited to, tobramycin, netilmycin, erythromycin, bacitracin, azithromycin, ciprofloxacin, gatifloxacin, gentamycin sulfate, levofloxacin, moxifloxacin hydrochloride, ofloxacin, sulfacetamide sodium, Polymyxin B sulfate, sulfacetamide, neomycin sulfate, bacitracin zinc, and gramicidin.

The liquid crystalline drug delivery system described above can be formulated with a hydrophobic drug. Examples of hydrophobic drugs include, but are not limited to, ROCK inhibitors, EGFR inhibitors, A-1 agonists, PARP inhibitors, SOD mimetics, PPAR agonists, WNT inhibitors, SYK-specific inhibitors, JAK-specific inhibitors, SYK/JAK or Multi-Kinase inhibitors, MTORs, STAT3 inhibitors, VEGFR/PDGFR inhibitors, c-Met inhibitors, ALK inhibitors, mTOR inhibitors, PI3Kδ inhibitors, PI3K/mTOR inhibitors, p38/MAPK inhibitors, macrolides, azole derivatives, prostaglandins, NO-releasing agents, peptides, NSAIDs, steroids, antibiotics, antivirals, antifungals, antiparsitic agents, blood pressure lowering agents, cancer drugs or anti-neoplastic agents, immunomodulatory drugs, diagnostic agents, and anti-oxidants.

Combinations of any of the above-mentioned APIs can also be incorporated into the liquid crystalline drug delivery system.

Alternatively, the liquid crystalline drug delivery system can be formulated without an API and administered for treating ocular conditions in which tear production is impaired or absent.

Without further elaboration, it is believed that one skilled in the art can, based on the description above, utilize the present invention to its fullest extent. The specific examples below are to be construed as merely illustrative, and not limitative of the remainder of the disclosure in any way whatsoever.

EXAMPLES

Example 1

Optimization of Process Development

As mentioned above, the nanoparticles (Phase I) are the API-containing portion of the formulation. The API is dissolved in a mixture of membrane-mimetic excipients that are co-soluble and also solubilize the API. The excipients used should be generally regarded as safe (GRAS) and US FDA-approved for ophthalmic use. A high solubility of API in Phase I will ensure a high concentration of the API in the final nano-dispersion. Phase I, containing at least one hydrophobic and one hydrophilic component, is also the dispersed phase in the liquid crystalline dispersion system.

Solubility of APIs were examined in different Phase I mixtures.

Initially, the solubility of fluticasone propionate was determined in 10 g of Phase I composed of a 7:3 (w/w) mixture of PHOSAL™ Medium Chain Triglycerides ("MCT") and polyethylene glycol-400 (PEG-400). MCT, a mixture of phosphatidylcholine and medium chain triglycerides, is the hydrophobic component and PEG-400 is the hydrophilic component in this exemplary Phase I. MCT and PEG-400 were added into a glass vial and the mixture was vortexed for 2 min. until the components formed a homogeneous mixture. Fluticasone propionate was added in an incremental manner and stirred at 850 rpm using a Scilogex MSH 280 Pro hot stir plate at a temperature of 37° C. Stirring was continued until saturation solubility was reached. Fluticasone propionate had a saturation solubility of 108.7 mg in 10 g of this Phase I mixture.

In order to increase the solubility of the fluticasone propionate in Phase I, mineral oil (Drakeol 600LT) was added into the composition. A Phase I containing MCT: PEG-400: mineral oil weight ratio of 7:2:1 was prepared as described above. The total amount of Phase I was 10 g. Fluticasone propionate was added in an incremental manner and the mixture was stirred for 5 min. and vortexed for 5 min after each addition of fluticasone propionate into the mixture. In this Phase I, 98.2 mg of fluticasone propionate dissolved completely in 37 min.

Another Phase I mixture containing PEG-400, polypropylene glycol (PPG), and cremophor in a weight ratio 2.9:7:0.1 was also evaluated. Cremophor was used because it is widely used as a co-solvent to enhance the solubility of poorly soluble drugs. The saturation solubility of the fluticasone propionate in this Phase I was 103.7 mg in 10 g after stirring at 990 rpm at 45° C. for 20 min.

The solubility of fluticasone propionate was also evaluated in 5% cetyl alcohol in ethanol. In this Phase I, 200.30 mg of fluticasone propionate was completely dissolved in 10 g when stirred at 1200 rpm for 2 min at 45° C.

Another Phase I mixture was produced containing 30% w/w PEG-400, 60% w/w PPG, 5% w/w MCT, 0.25% w/w cetyl alcohol, and 4.75% w/w ethanol. In 10 g of this Phase I, 180 mg fluticasone propionate dissolved completely after stirring at 1280 rpm for 15 min. at 45° C.

A different API, namely, triamcinolone acetonide was also tested with this Phase I. It was found that 220 mg of triamcinolone acetonide dissolved in 10 g of Phase I after stirring at 1280 rpm for 20 min at 45° C. Triamcinolone acetonide is a non-steroidal anti-inflammatory drug having low aqueous solubility.

Further modifications of Phase I were tested with the aim of enhancing API solubility further. To achieve this aim, additional hydrophobic components were introduced into Phase I.

A Phase I containing 30% w/w PEG-400, 20% w/w PPG, 0.5% w/w cetyl alcohol, 9.5% w/w ethanol, 5% w/w MCT and 35% w/w Castor oil was produced. Triamcinolone acetonide was added incrementally and the mixture stirred at 840 rpm using a Scilogex MSH 280 Pro set to 45° C. The saturation solubility for triamcinolone acetonide in 10 g of this Phase I was 230 mg.

Phase II is the aqueous phase, into which Phase I is poured, pumped, or injected, and subsequently mixed. Phase II, an aqueous solution containing only hydrophilic excipients, provides a buffer which maintains the pH and protects the API from pH-related instability in the final formulation. The optimization of Phase II was monitored by mixing it with Phase I to form Phase III. As mentioned above, Phase III is the term used for the emulsion that is formed when Phase I and Phase II are mixed using high energy processes.

A Phase II was formulated containing 0.5% w/w sodium hyaluronate, 0.63% w/w sodium chloride, 0.3% w/w sodium phosphate dibasic, 0.04% w/w sodium phosphate monobasic, and 98.56% w/w distilled $H_2O$ ($dH_2O$) at pH 6.5±0.1.

One part by weight of a Phase I containing 30% w/w PEG-400, 20% w/w PPG, 0.5% w/w cetyl alcohol, 9.5% w/w ethanol, 5% w/w MCT, and 35% w/w Castor oil was injected into 9 parts by weight of the Phase II at a flow rate of 0.5 g/min. to form Phase III. The mixing process was carried out using a Heilscher UP200S ultrasonic processor coupled with a sonotrode S3 microtip, with the processor set to 25% amplitude and 0.5 cycle. The Phase II was contained within a jacketed vessel set to 32° C.

The mean particle size of this Phase III, as measured by a Horiba LA952 particle analyzer, was found to be 26 μm. The emulsion produced by this process was not uniform in particle size; the variance for particle size distribution was 2157.60.

In an attempt to reduce the non-uniformity and large particle size of Phase III, polyethylene glycol stearates (PEG-stearates) were added to Phase I. PEG-stearates are mixtures of distearate esters of mixed macrogols (polyoxyethylene polymers) and corresponding free glycols. They are typically used as emulsifying and solubilizing agents in pharmaceutical compounds. Additionally, to achieve higher levels of hydrophobic content and to avoid high levels of ethanol in the formulation, a greater amount of MCT was used, and cetyl alcohol was used as described above. In order to avoid the clumping of cetyl alcohol at lower temperatures, the hydrophobic components were mixed at 67° C. at 250 rpm. A Phase I was produced that contains 28% w/w PEG-400, 10% w/w PPG, 10% w/w cetyl alcohol, 10% w/w Phosal MCT, 2% w/w PEG-stearate and 40% w/w Castor oil. This Phase 1(1 part by weight) was injected into 5 parts by weight Phase 11 (0.5% w/w sodium hyaluronate, 0.63% w/w sodium chloride, 0.3% w/w sodium phosphate dibasic, 0.04% w/w sodium phosphate monobasic, 98.56% w/w dH$_2$O) at a flow rate of 0.5 g/min to form a Phase III. The mixing process was carried out as described above with the ultrasonic processor set to 25% amplitude and 0.5 cycle. The Phase II was housed in a jacketed vessel set to 25° C. The mean particle size of the Phase III was found to be 30 μm. The emulsion produced by this process was better in uniformity of particle size, the variance for particle size distribution being 653.4, but the particle size had increased.

To further reduce the particle size, the ratio between Phase I and Phase II was varied while keeping their compositions constant. To form a Phase III, one part by weight of Phase I and 15 parts by weight of Phase II (both described in the previous paragraph) were mixed using the ultrasonic processor set to 30% amplitude and 1 cycle. The Phase II was housed in a jacketed vessel set to 25° C. The emulsion produced by this modified process was better in uniformity of particle size, with a variance for particle size distribution of 6.35 and a mean particle size of 3.6 μm. In this modification, the amplitude setting on the ultrasonic processor was 30%, as opposed to 25% described above. Despite the increased amplitude employed, the temperature of the final Phase III after sonication was found to be lower than the Phase III emulsions having a 1:5 ratio between Phase I and Phase II.

Thus, two factors were found to affect the particle size in a favorable manner, a lower Phase III temperature and a lower Phase I to Phase II ratio.

Lowering the ratio of Phase I to Phase II from 1:5 to 1:15 would have the effect of diluting the concentration of an API in the final formulation. Therefore, additional Phase I/II ratios were tested that would not lower the drug concentration as much as the 1:15 ratio.

The composition of Phase I and Phase II mentioned above were kept unchanged A Phase III was formed from a 1:11 ratio of Phase I to Phase II. Again, the mixing process was carried out using the ultrasonic processor set to 30% amplitude and 1 cycle. The Phase II was housed in a jacketed vessel set to 25° C. The mean particle size of the Phase III thus produced was 5.87 μm, with a variance of particle size distribution of 86.30. The ratio between Phase I and Phase II played an important role in the size of particles in the emulsion. A ratio that provides an optimal concentration of the drug (without diluting it too much) is of paramount importance in forming an efficient drug delivery system.

As mentioned above, keeping the temperature of Phase III low was an important factor to yield smaller particle sizes. Additionally, increasing the sonication duration was another factor. Increasing the duration of sonication is problematic as this leads to an increase in Phase III temperature. This increase, in turn, contributes to the increased particle size. To avoid an increase in the particle size due to a rise in temperature, bath sonication of the Phase III was introduced into the process.

The composition of Phase I and Phase II were kept unchanged and the phase ratio was kept at 1:11. Phase II was housed in a jacketed vessel set to 25° C. The ultrasonic mixing process was carried out as described above using a 30% amplitude and 1 cycle to form Phase III. The Phase III thus formed was subjected to 15 min. of bath sonication. The mean particle size of the Phase III was 5.48 μm with a variance of particle size distribution of 8.23. The temperature of Phase III was 28° C., indicating that the Phase III temperature remained relatively constant. The addition of a bath sonication process in the formulation development was a favorable change, as the particle size remained the same, while there was a reduction in the variance from 86.30 to 8.3, pointing to an increase in uniformity. In the case of liquid crystalline nanoemulsions, it has been observed that the presence of larger particles, as evidenced by a large variance, in the emulsion leads to coalescence and eventually phase separation in the emulsion. As such, the variance is also an indicator of stability.

Various surfactants were tested in an attempt to further reduce particle size. Tyloxapol, a nonionic liquid polymer of the alkyl aryl polyether alcohol type and a surfactant used to aid liquefaction, was added above its critical micelle concentration (CMC) of 0.018 mM to Phase II.

The composition of Phase I was kept unchanged (28% w/w PEG-400, 10% w/w PPG, 10% w/w cetyl alcohol, 10% w/w Phosal MCT, 2% w/w PEG-stearate, 40% w/w Castor oil) and Phase II was formulated with 0.5% w/w sodium hyaluronate, 0.63% w/w sodium chloride, 0.3% w/w sodium phosphate dibasic, 0.04% w/w sodium phosphate monobasic, 4% 0.1 mM tyloxapol solution, and 98.56% w/w dH$_2$O. Phase II was housed in a jacketed vessel set to 25° C. A Phase III was formed from a 1:11 Phase I to Phase II ratio by first mixing ultrasonically as described above with the processor set to 30% amplitude and 1 cycle. The Phase III mixture was subjected to 15 min. of bath sonication. The mean particle size of the Phase III thus formed was 1.81 μm, with a variance of particle size distribution of 1.02, indicating that the emulsion had a uniform particle size. The temperature of the Phase III was consistently 29° C., indicating that the temperature remained nearly unchanged. The addition of tyloxapol in the formulation development was favorable, as the particle size decreased by 600%, and there was a reduction in the variance from 8.3 to 1.02, indicating a stable emulsion.

Another surfactant that was tested was polysorbate 80. Polysorbate 80 was used below its CMC. The composition of Phase I was kept unchanged, while Phase II was formulated with 0.5% w/w sodium hyaluronate, 0.63% w/w sodium chloride, 0.3% w/w sodium phosphate dibasic, 0.04% w/w sodium phosphate monobasic, 0.00015% w/w polysorbate 80, and 98.56% w/w dH$_2$O. The Phase II was housed in a jacketed vessel set to 25° C. The ratio of Phase I to Phase II was kept at 1:11. The mixing process was carried out as described in the preceding paragraph. After the formation of Phase III, it was subjected to 15 min. of bath sonication. The mean particle size of Phase III was 53.75 μm, with a variance of particle size distribution of 6.05, indicating that the Tween addition below its CMC did not reduce the particle size.

A similar study was conducted to evaluate the effect on particle size of tyloxapol below its CMC. The presence of tyloxapol did reduce the particle size as compared to the Phase III emulsion produced with polysorbate 80 below its CMC. Moreover, this Phase III showed good uniformity in particle size, indicating a stable formulation.

Experiments were conducted to evaluate a synergistic effect of temperature and tyloxapol. These experiments were conducted at lower temperature, which was achieved by setting the Phase II jacketed vessel to 15° C. The resultant Phase III temperature after sonication was 22° C. Although a lower Phase III temperature was achieved, the size of the particles was 7.14 μm with a variance of 136.18, both values larger than those obtained at higher temperatures. The increase in particle size was attributed to the presence of sodium hyaluronate, which increases the viscosity of the Phase II at lower temperature. Thus, the presence of a stabilizer was eclipsed by the temperature of the process, and the temperature of the process proved to be a more important factor for the emulsion.

Another set of studies were conducted to evaluate the effect of sonication intensity on the particle size. It was observed that when the mixing process was carried out as above using the ultrasonic processor set to 40% amplitude (as opposed to 30% described above) and cycle 1, the mean particle size was reduced to 2.41 µm with a variance of 1.58. It was evident that higher sonication leads to smaller particle size. Additionally, it was observed from a series of experiments that sonication intensity played a more important role than the temperature of the Phase III mixing phase in determining particle size.

Since higher ultrasonic amplitude was found to be a favorable factor, the ultrasonic intensity was raised to 60% amplitude at cycle 1. The phase ratio was reduced to 1:10 (Phase I to Phase II), instead of 1:11, and the Phase II was housed in a jacketed vessel set to 25° C. After the formation of Phase III, it was subjected to 15 min. of bath sonication. The mean particle size was found to be 1.09 µm, and the emulsion was quite uniform with a variance of only 0.2116.

A series of experiments were carried out to further evaluate the effect of sodium hyaluronate, i.e., the sodium salt of hyaluronic acid, which is a glycosaminoglycan found in various connective, epithelial, and neural tissues. Sodium hyaluronate, a long-chain polymer containing repeating disaccharide units of sodium-glucuronate-N-acetylglucosamine, occurs naturally on the corneal endothelium. Sodium hyaluronate was introduced into Phase II for two reasons: (a) it functions as a tissue lubricant and facilitates wound healing and (b) it increases the viscosity of the formulation, thereby increasing the contact time between the delivery system and the target organ. The composition of Phase I was kept unchanged (28% w/w PEG-400, 10% w/w PPG, 10% w/w cetyl alcohol, 0% w/w MCT, 2% w/w PEG-stearate, 40% w/w Castor oil). Various concentrations of sodium hyaluronate were added to Phase II (0.63% w/w sodium chloride, 0.3% w/w sodium phosphate dibasic, and 0.04% w/w sodium phosphate monobasic, dH$_2$O). The results are shown in Table 1 below. It was observed that adding 0.4% w/w sodium hyaluronate to Phase II resulted in emulsions with lower particle sizes (50% of particles below 1 µm, i.e., D50<1 µm), while other concentrations of sodium hyaluronate resulted in particle sizes above 1 µm.

TABLE 1

Particle size distribution as a function of sodium hyaluronate concentration.

| HA (%) | D50 (µm) | D90 (µm) | mode (µm) |
|---|---|---|---|
| 0.1 | 1.02 | 1.78 | 1.09 |
| 0.2 | 1.18 | 1.72 | 1.20 |
| 0.3 | 2.3 | 4.39 | 2.41 |
| 0.4 | 0.9 | 1.49 | 0.9 |
| 0.5 | 1.02 | 1.78 | 1.09 |

Values shown are the particle size distributions (µm).
D50 = 50% of the particles are smaller than the value shown;
D90 = 90% of the particles are smaller than the value shown;
mode = statistical mode.

To further reduce the size of the particles in the emulsion, high shear mixing was introduced to the process. A Silverson L5MA mixer fitted with a high shear screen was used to mix Phase I and Phase II.

In a specific example, the composition of Phase I was 27% w/w PEG-400, 10% w/w PPG, 10% w/w cetyl alcohol, 10% w/w MCT, 2% w/w PEG-stearate, 40% w/w castor oil, and 1% w/w dexamethasone. The method of preparation of Phase I was modified from the above in order to incorporate the dexamethasone. The hydrophobic components were weighed and mixed at 50-55° C. to form a homogenous mixture. The hydrophilic components were then added and the mixture was continuously stirred to homogeneity. Finally, the dexamethasone was added and the mixing continued at 50-55° C. until the drug dissolved completely, resulting in a clear solution.

Phase II contained 0.4% w/w sodium hyaluronate, 0.63% w/w sodium chloride, 0.3% w/w sodium phosphate dibasic, 0.04% w/w sodium phosphate monobasic, 0.28% w/w PEG-stearate, 0.14% w/w polysorbate 80, and 98.21% w/w dH$_2$O.

To form 550 g of Phase III with a Phase I/Phase II ratio of 1/10, 500 g of Phase II was poured into a jacketed vessel set at 25° C. Phase 1 (50 g) at 39° C. was injected into Phase II at 0.5 g/min. (±0.1), while being mixed with a high shear screen at 10,000 rpm for 15 min. The mixer was reduced to 6000 rpm for the next 60 min. The mean particle size of Phase III thus formed was 0.85 µm (±0.44) with a variance of 0.196.

To improve the formulation further, the compositions of Phase I and Phase II described in the preceding paragraph were modified by raising the concentration of PEG-stearate in Phase I to 3% and omitting it from Phase II. Additionally, tyloxapol was added to Phase II at 0.3% w/w.

To produce 100 g of Phase III with a Phase I/Phase II ratio of 1/10, 90 g of Phase II was cooled prior to the mixing step to reduce the overall temperature of the process, after which it was poured into a jacketed vessel set at 15° C. Phase I (10 g) at 50° C. was injected into Phase II at 0.5 g/min (±0.1), while being mixed by Silverson L5MA mounted with emulsor screen at 6,000 rpm for 60 min. and 10,000 rpm for the next 15 min. at 30° C. The mean particle size of Phase III was 4.58 µm (±9.58) with a large variance of 91.58. Since very large particles were present, the head of the mixer was changed from an emulsor screen to a square holed high shear screen, as the latter provided more shear. The emulsion was further mixed for an additional 5 min. Mixing with the high shear screen reduced the mean size of the particles to 0.68 µm (±0.38)

The osmolality of the formulations is an important factor in the formulation development. When measured, the osmolality of the formulation described in the preceding paragraph was found to be 360 mOsm/kg. To reduce the osmolality of the formulation, the amount of PEG-400 was reduced to 20% w/w and the amount of PEG-stearate was increased to 7% w/w. Moreover, sodium hyaluronate was removed, as it increased the viscosity of Phase II, thereby contributing to larger particle size during mixing.

A 100 g amount of Phase III with a Phase I/Phase II ratio of 1/10 was formed by mixing 500 g of Phase II in a jacketed vessel set at 25° C. with 50 g of Phase I at 50-55° C. The Phase I was injected into Phase II at 1.0 g/min (±0.1) while being mixed with a high shear screen at 700 rpm for 15 min. at 25° C., 6000 rpm for 60 min, at 19° C., followed by 10,000 rpm for 10 min. at 30° C. The mean particle size of Phase III was 0.141 µm (±13.38) with a large variance of 184.14.

The flow rate of Phase I into Phase II is an important factor that affects the particle size of the Phase III formulation. This was more evident in the formulation development process that employed high shear mixing. A series of experiments was carried out to evaluate the effect of Phase I flow rate on the particle size of the Phase III emulsion. Variance was considered as a measure of stability instead of mean, mode, or median size, as variance is an indicator of the overall uniformity of the emulsion. For example, if the emulsion has a mean particle size of 0.1 µm and a variance of 2.0 µm, it indicates that the emulsion has a small population of particles that are larger than desired and their presence may eventually lead to coalescence and phase separation. The results are shown in Table 2 below. It is evident that increased flow rate led to a higher variance, i.e., low stability.

TABLE 2

Variance as a function of flow rate

| Flow rate (g/min.) | variance |
| --- | --- |
| 0.475 | 0.75 |
| 1.04 | 2.46 |
| 2.07 | 9.54 |
| 2.08 | 22.75 |
| 6.57 | 197.96 |

There was a considerable difference in particle size between formulations prepared with various mixing processes. As described above, three different mixing protocols were used in the development of the formulations. Mixing Phase I and Phase II by high shear mixing resulted in the percentage of particles below 200 nm consistently higher than 80%. Mixing Phase I and Phase II by sonication alone produced formulations having less than 0.8% of particles of 200 nm or less, while a combination of sonication and mixing resulted in formulations having 12-50% of particles less than 200 nm in size.

Various APIs were used to test the feasibility of this drug delivery platform. It was found that the platform was effective for producing nanodispersions using a number of poorly aqueous soluble non-steroidal anti-inflammatory drugs. Exemplary drugs are as follows, presented with their corresponding D50 and D90 values: dexamethasone (D50=0.139 µm; D90=0.170 µm), triamcinolone acetonide (D50=0.134 µm; D90=0.197 µm), and fluticasone propionate (D50=0.141 µm; D90=0.181 µm).

Example 2

Analysis Methods

Imaging of a 20 µL droplet of the dispersions was performed by placing it on a microscope slide and covering it with a glass coverslip, taking care to maintain the integrity of the emulsion. The dispersions was examined under crossed polarizers using a 100× objective of an Olympus BX51P Polarizing Light Microscope, under an oil-drop. Both drug-containing and drug-free dispersions were examined.

Particle sizing was carried out by adding approximately 20 µL of the Phase III dispersion in a solution of 2% w/w glycerin, 0.1% w/w sodium pyrophosphate decahydrate. Particle size distribution of the Phase III nano-dispersions were measured using a Horiba LA-950V2 particle size analyzer at room temperature, i.e., 22-25° C.

Encapsulation efficiency (mg/G) was measured by placing 1.0 g of drug-containing Phase III into a 1.5 mL centrifuge tube and centrifuging it at 6000 rpm for 10 minutes using an Eppendorf Centrifuge 5145D at room temperature. 100 µL of the centrifugate was transferred to an HPLC vial containing 900 µL of 75% acetonitrile/25% water. The samples were measured for concentration of drug, e.g., dexamethasone, by HPLC at $\lambda_{max}$=239 nm. The concentration was calculated as mg drug per g of the Phase III dispersion.

In-vitro drug release was determined at 37° C., pH 7.4 as follows: The Phase III dispersion (1 g) was transferred into a Spectra/Pore Float-A-Lyzer G2 dialysis device, which was then placed into a 50 mL locking centrifuge tube containing 40 g of 1% hydroxylpropyl-β-cyclodextrin (HP-β-CD) in phosphate buffer at pH 7.4, 37° C. The entire assembly was loaded onto a Robbins Scientific Model 400 rotating incubator. At each time point, 1 mL of sample was retrieved and fresh buffer added to replace the volume removed. Samples were measured for drug content using HPLC at $\lambda_{max}$=239 nm.

Ex-vivo corneal permeability testing is a useful tool to screen formulations for their ability to penetrate ocular tissues. Using freshly excised cornea, formulations can be tested for their ability to diffuse across the cornea membrane. The ability to diffuse through biological membranes is directly related to the formulation excipients, its physical state (e.g., suspension, solution, emulsion, dispersion) and its partition coefficient (P) and log P.

Fresh calf eyes were obtained from a nearby slaughterhouse and the corneas carefully excised using sterile technique. The corneas must be freshly excised and used within 1-2 hours. The corneas were excised in a sterilized laminar flow hood, in a Class 100 environment. The excisions were performed by first draining the aqueous humor followed by carefully cutting out the cornea using a scalpel for the initial incision; forceps and scissors were used to cut the remaining tissue. The excised cornea was stored in a petri dish with a small amount of a hydrating solution containing, by weight, 0.1% glutathione, 0.051% disodium phosphate, and 99.45% $H_2O$ at a pH of 7.0.

The solubility of the API in the receptor fluid is very critical in corneal permeability experiments. The saturated solubility of the drug in the receptor fluid must be much greater than the total theoretical concentration of the drug in the receptor solution. The composition of a typical receptor fluid is, by weight, 1% HP-β-CD, 0.051% disodium phosphate, 0.017% sodium phosphate monobasic, and 98.55% $H_2O$.

Corneal permeability studies were performed using a Franz-Cell diffusion chamber system. The Franz-Cell system consists of 6 in-line jacketed cells mounted on a single unit with individual magnetic stir plates, with each cell connected to the main system water jacket. The jacket was maintained at 37° C. for the duration of the experiment using a recirculating heating bath. Each cell consists of a donor cell on the top where a known volume of the formulation is pipetted and a receptor cell with a sampling side arm below. The joint between the donor and receptor cell is upward-convex, mimicking the shape of the cornea. Each receptor cell holds 5 mL of receptor fluid, and each donor cell holds 200 µL of the formulation being studied.

The receptor fluid was added to each receptor cell using a syringe equipped with a needle. The solution was slowly added, until there was a convex meniscus on the donor cell joint. The volume was recorded, and the remaining cells filled.

After weighing the cornea, it was placed on top of the receptor-donor cell joint using a pair of forceps, with care taken to ensure that there were no folds in the cornea and no bubbles. Once in place, donor cell caps were attached carefully, and locked in place with a metal clip.

Samples were added in rapid succession by depositing 200 µL of the formulation into each donor chamber using a calibrated pipet and the times recorded. The donor chamber and sampling arm were sealed to ensure no significant evaporation has occurred.

Samples were withdrawn from the receptor cells at 2, 4, 6, 7, and 22 hours. The samples were analyzed for API content by HPLC as described above.

Flux (J) is the amount of drug crossing the membrane per unit time. It is given in units of mass/area/time. Flux can be calculated by the formula: $J=Q/(A \cdot t)$, where Q is the quantity of compound traversing the membrane in time t, and A is the area of exposed membrane in $cm^2$. The units for flux are weight (micrograms)/$cm^2$/min.

Example 3

Preparation of Nanostructured Dispersions Containing 0.1% Fluticasone Propionate Preparation of Phase I A 30 g amount of Phase I was prepared by adding 3 g of PHOSAL® Mixed Chain Triglycerides ("MCT"), 3 g of cetyl alcohol, and 11 g of castor oil into a pre-tared glass beaker. The mixture was heated to 55° C. with continuous stiffing on a hot plate to form a homogenous mixture. To this mixture, 6 g of polyethylene glycol-400, 3 g of polypropylene glycol, 2.1 g of PEG-40-stearate, 0.666 g of Poloxamer 407, 0.3 g of Tyloxapol and 0.3 g of Tween 80 were added, followed by stiffing at 55° C. After ensuring a homogenous mixture was achieved, the heat component of the stir plate was switched off. Fluticasone propionate (0.24 g) was added to the mixture once it cooled to 40° C.-45° C. The mixture was stirred until the fluticasone propionate was completely solubilized into a homogenous, clear solution with no visible particulates, thereby forming Phase I.

Preparation of Phase II

A 300 g amount of Phase II was prepared from 0.051 g of sodium phosphate monobasic, 0.156 g of sodium phosphate dibasic, and 299.796 g of distilled $H_2O$ ($dH_2O$) were added into a tared glass beaker. This mixture was stirred until the sodium salts were completely dissolved, thereby forming Phase II. The pH of Phase II was 7.3.

Preparation of Phase III

Phase III is the term used for the dispersion that is formed when Phase I and Phase II are mixed using high energy processes. In this example, high shear mixing was used to obtain the final dispersion.

To obtain 100 g of Phase III, 10 g of Phase I was injected into 90 g of Phase II at a flow rate of 1 g/min and the mixture continuously mixed using a Silverson L5MA high shear laboratory mixer. During the injection, Phase I was maintained at 40-45° C. and Phase II was cooled to 8° C. More specifically, Phase II was poured into a jacketed vessel connected to a chiller set at −10° C.

Two mixing speeds were used to obtain the final dispersion, i.e., Phase III. A high speed of 7,500 RPM was used when Phase I was being injected into Phase II. Upon complete addition of Phase I, the mixing speed was reduced to 5,040 RPM for the remainder of the mixing period. The mixing was carried out for a total of 150 minutes. In this example, the high mixing rate was used for the first ten minutes, and then the lower rate was used. The final concentration of fluticasone propionate was 0.1% by weight of Phase III.

The statistical mode of particle size in the dispersion was 120 nm. The middle of the dispersion was 122 nm, and 85% of all the particles were smaller than 300 nm. The dispersion appeared milky white, homogeneous, and stable upon storage at room temperature.

When examined by polarized optical microscopy, the dispersion displayed a unique nanostructure, akin to a liquid crystalline state. The dispersed phase is semi-solid, rendered so by the intercalation of Phase II into Phase I. The nano-size of the dispersion renders it suitable for permeation into tissues.

Example 4

Preparation of Nanostructured Dispersions Containing Dexamethasone

Preparation of Phase I

A 30 g amount of Phase I was prepared by mixing 3 g of MCT, 3 g of cetyl alcohol, and 12 g of castor oil in a glass beaker. This mixture was heated to 55° C. with continuous stiffing on a hot plate to form a homogenous mixture To this mixture, 6 g of polyethylene glycol-400, 3 g of polypropylene glycol, 2.1 g of PEG-40-stearate, and 0.6 g of Poloxamer 407 were added, followed by continued stirring at 55° C. After a homogenous mixture was formed, the heat component of the stir plate was switched off. Dexamethasone (0.3 g) was added to the mixture once the mixture cooled to 40-45° C. The mixture was stirred until the dexamethasone was completely solubilized.

Preparation of Phase II

A 300 g amount of Phase II was prepared by mixing 0.051 g of sodium phosphate monobasic, 0.156 g of sodium phosphate dibasic, and 299.796 g of $dH_2O$ in a glass beaker. This mixture was stirred until the sodium salts were completely dissolved. The pH of Phase II was 7.3.

Preparation of Phase III

Phase III was formed as follows: 90 g of Phase II was cooled to 8° C. by pouring it into a jacketed vessel connected to a chiller set at −10° C. A 10 g amount of Phase I, maintained at 40-45° C.; was injected into Phase II at a flow rate of 1 g/min with continuous mixing using a Silverson L5MA high shear mixer.

Like Example 3 described above, two mixing speeds were used to obtain the final dispersion, i.e., Phase III. Initially, a high speed of 10,000 RPM, i.e., primary mixing, was used while Phase I was being injected into Phase II. After all of the Phase I was introduced, the mixing was carried out at a lower rate of 5,040 RPM, i.e., secondary mixing, for the remainder of the mixing period. The mixing was carried out for a total of 150 min, where the high mixing rate was used for the first ten minutes followed by the lower rate. The final concentration of dexamethasone was 0.1% by weight of Phase III.

Analysis of the dispersion revealed that the median (d50) of the particle size distribution was 143 nm, the mode was 141 nm, and 90% of the dispersed nano-structured particles were smaller than 245 nm. The nanostructured dispersion was stable over time at room temperature. When examined microscopically, the dispersion demonstrated an ordered microstructure, indicative of an ordered, but liquid-like state.

Additional analysis revealed that the dexamethasone was encapsulated at 0.845 mg/G. An in-vitro drug release assay indicated that at least 25% of the dexamethasone was released over 3 hours, indicating a highly bioavailable formulation.

The corneal permeability of the nanostructured formulation of 0.1% dexamethasone was tested as described above.

Approximately 35% of the dexamethasone applied to the corneas was released into the receptor solution over a 22 hour period, indicating a high bioavailability of the formulation. In contrast, a suspension of dexamethasone tested in the same assay displayed a fairly low corneal permeability of <5% in 22 hours. Additionally, after the diffusion study was complete, the corneas were extracted in acetonitrile and analyzed for dexamethasone content. A substantial depot-like effect was observed in the corneas treated with the formulation, indicating that a sustained release effect can be achieved with this formulation. More specifically, the amount of dexamethasone extracted from the corneas averaged 35% of the total initially loaded onto the corneas.

Example 5

Preparation of Nanostructured Dispersions Containing Loteprednol Etabonate

Preparation of Phase I
A 30 g amount of Phase I was prepared as described above in EXAMPLE 4, except that loteprednol etabonate (0.3 g) was added instead of dexamethasone.
Preparation of Phase II
A 300 g amount of Phase II was prepared also as described in EXAMPLE 4 above.
Preparation of Phase III
Phase III was formed with a 1:9 ratio (w/w) of Phase I to Phase II as described above in EXAMPLE 4. The final concentration of loteprednol etabonate was 0.1% by weight of Phase III.

Analysis of the dispersion revealed that the median (d50) of the particle size distribution was 159 nm, the mode was 160 nm, and 90% of the dispersed nano-structures were smaller than 303 nm. The nanostructured dispersion was stable for at least 60 days at room temperature, with no settling or degradation observed. When examined microscopically, the dispersion demonstrated an ordered microstructure, indicative of an ordered, but liquid-like state.

Additional analysis indicated that the amount of loteprednol etabonate encapsulated was 1.24 mg/G. The drug had an in vitro release of 35% in 3 hours. Surprisingly, corneal permeability of the loteprednol etabonate was 36% in 22 hours, as opposed to 8% for a commercially available formulation of this drug, i.e., Lotemax® gel.

Example 6

Preparation of Drug-Free Nanostructured Dispersions by High Shear Mixing and Microfluidization Preparation of Phase I
A 70 g amount of Phase I was prepared by mixing 7.01 g of MCT, 7.01 g of cetyl alcohol, and 28 g of castor oil in a glass beaker. This mixture was heated to 55° C. with continuous stirring on a hot plate to form a homogenous mixture To this mixture, 7.07 g of polyethylene glycol-400, 7.07 g of polypropylene glycol, and 4.97 g of PEG-40-stearate were added, followed by continued stirring at 55° C. After a homogenous mixture was formed, the heat component of the stir plate was switched off.
Preparation of Phase II
A 700 g amount of Phase II was prepared by mixing 0.21 g of tyloxapol, 0.11 g of Tween 80, 1.441 g of citric acid monohydrate, 6.9688 g of sodium citrate dehydrate, 0.140 g of Poloxamer 407, and 691.68 g of dH$_2$O were added into a glass beaker. This mixture was stirred until the salts are completely dissolved. The pH of Phase II was 6.0.
Preparation of Phase III
A total of 600 g of Phase III was formed as follows: 540 g of Phase II was maintained at 50-55° C. in a jacketed vessel connected to a chiller set at 50° C. A 60 g amount of Phase I, maintained at 50-55° C.; was poured into Phase II and mixed for 15 min. using a Silverson L5MA high shear mixer set at 7500 RPM. The resulting dispersion was passed 4 times through a microfluidizer at a pressure of 28 psi.

Analysis of the dispersion revealed that the median (d50) of the particle size distribution was 176 nm, the mode was 207 nm, and 90% of the dispersed nano-structures were smaller than 358 nm. The nanostructured dispersion was stable over time at room temperature and, when examined microscopically, the dispersion demonstrated an ordered microstructure, indicative of an ordered, but liquid-like state. The microfluidization step resulted in a unimodal dispersion.

Example 7

Preparation of Drug-Free Nanostructured Dispersions by High Shear Mixing and Sonication Preparation of Phase I
A 70 g amount of Phase I was prepared as described above in EXAMPLE 6.
Preparation of Phase II
A 70 g amount of Phase II was prepared also as described above in

EXAMPLE 6.

Preparation of Phase III
A total of 600 g of Phase III was formed as follows: 540 g of Phase II was maintained at 40-45° C. in a jacketed vessel connected to a chiller. A 60 g amount of Phase I, maintained at 40-45° C.; was poured into Phase II and mixed for 15 min. using a Silverson L5MA high shear mixer set at 7500 RPM. The resulting dispersion was subjected to sonication with a Heilscher UP200S ultrasonic processor set to 50% amplitude using a sonotrode S3 microtip. The dispersion was sonicated three times, and an aliquot was taken after each time to monitor the effect of sonication.

Analysis of the dispersion revealed that the median (d50) of the particle size distribution was 167 nm, the mode was 140 nm, and 75% of the dispersed nano-structures were smaller than 316 nm. Additionally, the nanostructured dispersion was stable over time at room temperature and displayed an ordered microstructure when examined microscopically.

Example 8

Solubility of Fluticasone Propionate in Nanostructured Dispersions

Phase I was prepared containing PEG-400 at 20%, PPG at 10%, cetyl alcohol at 10%, MCT at 1% , PEG-stearate at 7%, poloxamer 407 at 2.22%, tyloxapol at 1%, polysorbate 80 at 1%, castor oil at 38%, and fluticasone propionate at 1-2%.

The composition of Phase II was sodium phosphate monobasic (0.017%), sodium phosphate dibasic (0.052%), sodium hyaluronate (0.15%), and dH$_2$O (99.78%).

Phase I was mixed with Phase II at a weight ratio of 1:9.

The concentration of fluticasone propionate achievable in this formulation was 0.1-0.2%. Notably, when fluticasone propionate is solubilized separately in each excipient and the solubilized contribution from each excipient added, the maximum concentration of fluticasone propionate expected is only 0.05%. Yet, the formulation surprisingly solubilized fluticasone propionate at 0.1-0.2% by weight.

It was also determined that the combined presence of cetyl alcohol and MCT provided enhanced solubilization, even though the solubility of fluticasone propionate in MCT is minimal (0.150 mg/ml). The solubility of fluticasone propionate in cetyl alcohol was 0.3 mg/ml. As just described, the final dispersion has a fluticasone propionate concentration of 1-2 mg/ml (0.1-0.2%).

Not to be bound by theory, it is likely that the enhanced solubility of the drug results from the synergistic self-assembly of the phases to form an intercalated ordered phase.

Example 9

Effect of Hydrophobicity of Phase I

In this example, cholesterol was added to obtain a higher concentration of hydrophobic excipients. The composition of Phase I was PEG-400 (20%), PPG (10%), cetyl alcohol (10%), cholesterol (2%), MCT (10%), PEG-stearate (5%), poloxamer 407 (2.22%), tyloxapol (1%), polysorbate 80 (1%), castor oil (36.9%), and fluticasone propionate (1-5%).

The composition of Phase II was sodium phosphate monobasic (0.017%), sodium phosphate dibasic (0.052%), sodium hyaluronate (0.15%), and dH$_2$O (99.78%).

Phase I was mixed with Phase II at a weight ratio of 1:9.

The final concentration of fluticasone propionate achievable in this formulation is 0.1-0.5% The maximum amount of fluticasone propionate expected to be solubilized by adding up the amount solubilized in each separate excipient is 0.06%.

Again, in this EXAMPLE 9, a higher concentration of a hydrophobic drug was achieved in the nano-dispersion than is theoretically possible for drug solubilization by each individual component of Phase I Example 10

In Vitro Drug Release from Nanodispersion

A nano-dispersion was produced using Phase I and Phase II described above in EXAMPLE 8 except that dexamethasone was incorporated instead of fluticasone propionate. Phase I was mixed with Phase II with a Silverson high shear homogenizer, with both Phases at a temperature between 40-45° C., followed by high pressure homogenization using a microfluidizer. The mixture was passed through the microfluidizer 1 to 5 times at room temperature. The resultant mixture was then mixed overnight (18-22 hours) with a Silverson high shear homogenizer at ~10° C. After mixing, the dispersion was stored between 2-5° C. for 22-24 hours.

A micro-dispersion was formed of the identical components by mixing Phase I and Phase II with an overhead Scilogix stir-paddle mixer at 1800 RPM for 2-3 hours. The temperature of each phase was 40-45° C. The micro-dispersion was not incubated at 2-5° C. for 22-24 hours.

Particle size measurements revealed that the D50 of the nanodispersion was between 100-250 nm while the D50 of the microdispersion was between 60-90 μm.

In-vitro cumulative release rates of dexamethasone from the nanodispersion and the microdispersion were determined in phosphate buffered saline, pH 7.4 at 37° C. The results indicated that 100% of the dexamethasone initially loaded in the microdispersion was released after 40 h. By contrast, only ~55% of the dexamethasone initially loaded in the nanodispersion was released over the same time period. A cumulative release of 50% of the initial amount of dexamethasone was measured by 10 h for the microdispersion as compared to 24 h for the nanodispersion.

The larger particles of the microdispersion have a larger diffusive path length for drug release. It was expected that the release from the microdispersion would be slower than from the nanodispersion. As such, this result was unexpected.

Again, not to be bound by theory, it is thought that the intercalated ordered nanostructure of the nanodispersion creates tortuous diffusive paths for the drug molecules to be released.

Example 11

Bioavailability Measured by Corneal Permeability

Four distinct formulations of fluticasone propionate (0.1%) were prepared to ascertain the parameters leading to improved bioavailability. Formulation I included all of the excipients listed above in EXAMPLE 8 except for MCT, cetyl alcohol, and sodium hyaluronate. Formulation II was the same as Formulation I but also included sodium hyaluronate. Formulation III was identical to that described in EXAMPLE 8. Formulation IV was identical to that described in EXAMPLE 9.

The four formulations were prepared following the same mixing protocols described in EXAMPLE 8. The four formulations were tested for corneal permeability as described above in EXAMPLE 2.

The results indicated that only 2.39% of the fluticasone propionate in Formulation I permeated through the cornea between 7-22 hours after application of the formulation to the cornea. Similarly, only 2.3% of the fluticasone propionate in Formulation II diffused through the cornea in 7-22 hours.

By contrast, 17% and 20% of the fluticasone propionate from Formulation III and Formulation IV, respectively, diffused through the cornea between 7 and 22 hours. Clearly, these two formulations demonstrated a greater bioavailability as compared to Formulations I and II, both lacking MCT and cetyl alcohol.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, a person skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

The invention claimed is:

1. A method for producing a liquid crystalline drug delivery system, the method comprising:
   forming a first solution containing a lipidic component and an alcohol, the first solution being maintained at a temperature of 40-55° C.;
   obtaining a second solution that includes a mucoadhesive hydrophilic polymer and a buffer, the second solution being aqueous and maintained at a temperature of 5-55° C.;
   mixing the first solution and the second solution to form a combined nano/micro-dispersion, the mixing accomplished by a high energy mixing process selected from sonication, high shear mixing, and a combination thereof;
   subjecting the combined nano/micro-dispersion to microfluidization at a temperature of −10° C. to room temperature to form a nano-dispersion; and
   incubating the nano-dispersion at 2-5° C. to form a liquid crystalline drug delivery system,
   wherein a weight ratio between the first solution and the second solution is 1:1 to 1:15, the lipidic component includes phosphatidylcholine and medium chain triglycerides, the alcohol is cetyl alcohol, and the mucoadhesive hydrophilic polymer is selected from the group consisting of sodium hyaluronate, xanthan gum, guar gum, carboxymethyl cellulose, 1-4 beta glucan, poly(ethylene oxide)-poly(propylene oxide)-poly(ethylene oxide), tamarind seed polysaccharide, sodium alginate, polycarbopol, polycarbophil, and a mixture thereof.

2. The method of claim 1, wherein the first solution further contains cholesterol, polyethylene glycol (PEG) 400, polypropylene glycol (PPG), PEG-stearate, poloxamer 407, tyloxapol, polysorbate 80, poly(lactic-co-glycolic acid), or castor oil.

3. The method of claim 1, further comprising dissolving at least one active pharmaceutical ingredient (API) into the first solution, wherein the at least one API is selected from the group consisting of fluticasone propionate, dexamethasone, betamethasone, budesonide, triamcinolone acetonide, methyl prednisolone, cortisone, beclometasone, fluticasone furoate, deoxycorticosterone acetate, loteprednol etabonate, difluprednate, fluorometholone, rimexolone, travoprost, azithromycin, moxifloxacin, netilmycin, nepafenac, diclofenac, difluprednate, posaconazole, prednisolone acetate, and a combination thereof.

4. A liquid crystalline drug delivery system, comprising nanoparticles dispersed in an aqueous solution, the nanoparticles including a lipidic component and an alcohol, the aqueous solution containing a mucoadhesive hydrophilic polymer and a buffer,
   wherein the lipidic component is present at 0.1-1% by weight of the system, the alcohol is present at 0.1-5% by weight of the system, the mucoadhesive hydrophilic polymer is present at 1-5% by weight of the system, the nanoparticles have a size of 40 nm to 900 nm, the system has a pH of 6-7.5, an osmolarity of 250-340 mOsm/L, and a viscosity of 200-1000 cP, the lipidic component includes phosphatidylcholine and medium chain triglycerides, the alcohol is cetyl alcohol, and the mucoadhesive hydrophilic polymer is selected from the group consisting of sodium hyaluronate, xanthan gum, guar gum, carboxymethyl cellulose, 1-4 beta glucan, poly(ethylene oxide)-poly(propylene oxide)-poly(ethylene oxide), tamarind seed polysaccharide, sodium alginate, polycarbopol, and polycarbophil, and a mixture thereof.

5. The liquid crystalline drug delivery system of claim 4, wherein the nanoparticles further include cholesterol, polyethylene glycol (PEG) 400, polypropylene glycol (PPG), PEG-stearate, poloxamer 407, tyloxapol, polysorbate 80, castor oil, PEGylated castor oil, poly(lactic-co-glycolic acid), or mixtures thereof.

6. The liquid crystalline drug delivery system of claim 4, further comprising an active pharmaceutical ingredient (API) at 0.01-0.5% by weight of the system, wherein the API is loaded in the nanoparticles and the API is an anti-inflammatory, a peptide, an anti-oxidant, an azole derivative, an anti-glaucoma drug, or a combination thereof.

7. The liquid crystalline drug delivery system of claim 4, further comprising an active pharmaceutical ingredient (API) at 0.01-0.5% by weight of the system, wherein the API is loaded in the nanoparticles and the API is selected from the group consisting of fluticasone propionate, dexamethasone, betamethasone, budesonide, triamcinolone acetonide, methyl prednisolone, cortisone, beclometasone, fluticasone furoate, deoxycorticosterone acetate, loteprednol etabonate, difluprednate, fluorometholone, rimexolone, travoprost, moxifloxacin, azithromycin, netilmycin, nepafenac, diclofenac, difluprednate, posaconazole, prednisolone acetate, and a mixture thereof.

8. A method for treating an ocular disorder in a subject, the method comprising identifying a subject having an ocular disorder and administering to an eye of the subject the liquid crystalline drug delivery system of claim 6.

9. The method of claim 8, wherein the ocular disorder is post-operative inflammation, inflammation, allergic rhinitis, allergic conjunctivitis, meibomian gland dysfunction, infection, conjunctivitis, keratitis, ulcers, blepharitis, glaucoma, uveitis, diabetic macular edema, diabetic retinopathy, age-related macular degeneration, endophthalmitis, choroidal neovascularization, tear duct dysfunction, corneal blebs, or dry eye disease.

10. The method of claim 8, wherein the liquid crystalline drug delivery system is administered by vitreous injection, by spraying into the eye, or as an eye-drop.

11. The method of claim 9, wherein the ocular disorder is blepharitis and the API is fluticasone propionate.

12. The method of claim 9, wherein the ocular disorder is allergic conjunctivitis and the API is loteprednol etabonate.

13. The method of claim 9, wherein the ocular disorder is post-operative inflammation and the API is dexamethasone.

14. The method of claim 9, wherein the ocular disorder is infection and the API is moxifloxacin.

15. The method of claim 9, wherein the ocular disorder is keratitis and the active pharmaceutical ingredient is an azole derivative.

16. The method of claim 9, wherein the ocular disorder is uveitis.

17. The method of claim 9, wherein the ocular disorder is glaucoma.

18. The method of claim 9, wherein the ocular disorder is diabetic retinopathy.

19. The method of claim 9, wherein the ocular disorder is age-related macular degeneration.

20. The method of claim 9, wherein the ocular disorder is choroidal neovascularization.

* * * * *